United States Patent [19]

Lundeen

[11] Patent Number: 4,676,801
[45] Date of Patent: Jun. 30, 1987

[54] FOOT ORTHOSIS AND PROCESS

[75] Inventor: Richard O. Lundeen, Zionsville, Ind.

[73] Assignee: Orthopedic Specialties, Inc., Indianapolis, Ind.

[21] Appl. No.: 497,075

[22] Filed: May 23, 1983

[51] Int. Cl.⁴ .............................................. A61F 2/66
[52] U.S. Cl. .................................................. 623/53
[58] Field of Search .................... 264/222, DIG. 30; 12/128 V, 134, 133 C; 623/27, 28, 29, 53, 54, 55, 56

[56] References Cited

U.S. PATENT DOCUMENTS

| 327,538 | 11/1885 | Dodworth | 12/114.2 |
|---|---|---|---|
| 1,691,054 | 11/1928 | Galterio | 12/128 V |
| 1,746,466 | 2/1930 | Galterio | 12/128 V |
| 1,753,857 | 4/1930 | Galterio et al. | 12/128 V |
| 2,000,340 | 5/1935 | Marca et al. | 12/128 V |
| 2,725,234 | 11/1955 | Cobbe et al. | 273/157 R |

OTHER PUBLICATIONS

Root et al., Biomechanical Examination of the Foot, vol. II, Clinical Biomechanics Corp., Los Angeles, 1977, pp. 173-201.
Lundeen, The Integrated Dual-Axis Functional Foot Orthosis, Ill. Coll. Podiatric Medicine, 1977.
Whitman, Orthopaedic Surgery, 5th Edition, Lea and Febiger, Philadelphia, 1917 (various pages).
Roberts, The Influence of the Os Calcis on the Production and Correction of Valgus Deformities of the Foot, Am. J. Orthop. Surg., Dec. 1916.
Silverman, Device for Heel Stabilization, Current Podiatry, Dec. 1960.
Henderson et al., UC-BL Shoe Insert: Casting and Fabrication, Bio-Mechanics Research Laboratory, the University of California, San Francisco and Berkley, Technical Report 53, San Francisco, The Laboratory, Aug. 1967.
Bick, Source Book of Orthopedics, Williams and Wilkins, Baltimore, 1948.
Knittel et al., The Effectiveness of Shoe Modifications for "Intoeing", Ortho. Clinics, 7:1010, Oct. 1976.
Godfrey, Heel Modifications as Aids in Rotational Control, Clin. Orthop., 4:120, 1954.
Wickstrom et al., Shoe Corrections and Orthopaedic Foot Supports, Clin. Orthop., 70:30, 1970.
Rose, Correction of the Pronated Foot, J. Bone Joint Surg., 44-B, 142, Aug. 1962.
Helfet, A New Way of Treating Flat Feet in Children, Lancet, 1:262, 1956.
Inman, UC-BL Dual Axis Ankle-Control System and UC-BL Shoe Insert, Bulletin of Prosthetics Research, Spring, 1969, pp. 130-145.

Primary Examiner—Richard J. Apley
Assistant Examiner—D. Isabella
Attorney, Agent, or Firm—Killworth, Gottman Hagan & Schaeff

[57] ABSTRACT

A positive casting for a human foot for use in making a foot orthosis is disclosed. The positive casting includes a main section, a rear section, and a front section. The rear section is movable with respect to the main section for correcting deformities in the rearfoot. The front section is movable with respect to the main section for correcting deformities in the forefoot. A mechanism is also provided for fixing together and adjustably positioning the three sections thus formed with respect to one another. The casting can include a first ray section cut from the front section and movable with respect to the front section for correcting deformities in the forefoot and first ray. A method is also disclosed for forming a foot orthosis which includes the improvement of sectioning a positive casting made of a foot into a main section, a front section, and a rear section. The main section, front section, and rear section are adjusted with respect to each other to correct for deformities in the foot. The relative positions of the main section, front section, and rear section are then fixed with respect to one another. An orthosis is then made by pressing or forming a formable material such as thermoplastic over the adjusted positive casting.

9 Claims, 9 Drawing Figures

FOOT ORTHOSIS AND PROCESS

This invention relates to a device and method for correcting foot deformities. More particularly, this invention relates to foot orthoses and methods for making foot orthoses.

Foot orthoses are therapeutic devices designed to correct deformities or prevent the patient from compensating for deformities such as forefoot and rearfoot varus and valgus, pes plano valgus, pes cavus, and other foot and lower extremity deformities. "Correct for deformities" as used in this application is used with the same scope as is normally used by podiatrists to encompass correction and reduction of and compensation for one or multiple deformities. Although foot orthoses are generally intended to prevent compensation for foot deformities, orthoses often can actually correct or reduce deformities in the foot. Successful correction of deformities is especially likely in younger patients. Typically, a foot orthosis is generally non-planar and sheet-like, conforming in shape to the plantar surface of the patient's foot. Orthoses are designed to fit in the patient's shoes between the patient's foot and the bottom surface of the inside of the shoe. Like eyeglasses, foot orthoses are individual to each patient, with each orthosis being fitted to correct for each patient's particular deformity.

The first step in forming an orthosis is for the physician or podiatrist to make a biomechanical examination of the patient's foot. In this biomechanical examination, the patient's foot is studied and measured to determine the particular deformity which affects the patient, and the best means for correcting for the deformity. The examination procedure is analogous to an examination performed by an opthamologist to determine the correct type of eyeglasses to correct for a patient's vision problems. A negative impression is then made of the patient's foot. From the negative impression, a positive casting is made of the patient's foot. Around this positive casting, an orthotic device is made. Most negative impressions are cast for with the patient's feet in neutral position. Neutral position is that position the foot is in when the subtalar joint is neither inverted nor everted and the midtarsal joint is dorsoflexed and everted to resistance on the subtalar joint.

Clinically, this position is usually attained by palpating, with the thumb and forefinger, the adjacent sides of the sinus tarsi and feeling for congruency of the talar head in the sinus. Once this has been attained, the practitioner grasps the fourth and fifth toe sulcus with his other hand and gently dorsoflexes the forefoot to resistance on the rear foot. Measurements are then taken between bisections of the lower one-third of the leg and heel, and heel and plane between the first and fifth metatarsal heads. Measurements in excess of two degrees varus or valgus represent deformities orthoses can be used to treat conservatively. Often other measurements must be taken, but these represent the most important measurements for prescribing the immediate invention.

The ability of an orthosis to perform its designated function depends on a thorough understanding on the part of the practitioner of the anatomy of the foot and the cooperative operation of the osseous, muscular, and neurological structures of the foot. The orthosis made according to the instant invention incorporates these biomechanical considerations into its design to effectively control foot deformities.

Often, a forefoot and rearfoot post will be applied to an orthotic to correct for the deformities of the foot. A post, as used in this context, is anything added to or incorporated into an orthotic device to either invert or evert a part of the foot.

The forefoot and rearfoot are posted by different techniques. It is necessary to understand the theories behind forefoot posting and rearfoot posting in order to appreciate the applicant's posting process for treating foot deformities.

The conventional type of podiatric orthosis is posted with a material such as an acrylic in two places on the thermoplastic orthosis. The rearfoot post is applied directly to the posterior surface of the thermoplastic on the heel and the forefoot post is applied to the distal aspect of the device and is placed proximal to the metatarsal heads.

Conventional foot orthoses utilize either extrinsic or intrinsic posting to prevent the foot from compensating for a particular deformity. Extrinsic posting is a posting procedure wherein acrylic or other material is added onto to the plantar surface of the orthosis to bring the dorsal, supporting surface of the orthosis up to the level of the foot. Intrinsic posting is posting in the plastic itself by bending the plastic to raise the level of the supporting, dorsal surface of the orthotic to the level of the patient's foot. Orthoses designed to prevent compensation for foot deformities with evaluation and posting determined by examining the foot around its neutral position are termed "functional" orthoses.

One type of functional orthosis is described by Root et al in *Biomechanical Examination of the Foot*, Vol. II, Clinical Biomechanics Corp., Los Angeles, 1977. With Root's orthosis, an extrinsic plaster post is applied directly to the plantar aspect of the positive casting made of the patient's foot. The Root orthosis serves to hold the forefoot around its neutral position by relatively increasing the sagittal plane height between the metatarsals and the supporting surface. The sagittal plane height generally refers to the height of the apex of the arch above a horizontal supporting surface such as a floor.

Another method for posting the forefoot is discussed in Lundeen, *The Integrated Dual-Axis Functional Orthosis*, Ill. Coll. Podiatric Medicine, 1977, wherein the applicant discusses a method of making an orthotic from a positive casting having a movable rear section. The rear section is formed by cutting a positive casting along a line which corresponds generally to a line passing obliquely between the fibular and tibial malleolei of the foot. The primary thrust of the rearfoot movable casting is to enable the practitioner to better correct for deformities in the rearfoot. The forefoot posting technique described in the 1977 article is a modification of a technique utilized by Root in which a plaster forefoot post is added directly to the positive impression in the direction of the deformity. This method of posting modified Root's methods by relatively increasing the saggital plane height between the midtarsal joints and the supporting surface.

Root also discloses the addition of an expansion to the medial aspect of the positive casting. The medial expansion increases the area of the plantar surface of the casting along its medial side. The medial expansion is added so that the orthosis will lie on the same plane as the plantar aspect of the foot. Root also adds a lateral expansion in order to accommodate for the increase in the displacement of the plantar fat pads when the foot is bearing weight. Subsequent to its introduction, the Root orthosis has undergone modifications, one of which is the raising of the medial expansion up to the level of the post. The applicant's prior orthosis made from a rearfoot movable casting improved upon this modification to provide for a gradual transition between the medial expansion and the plantar aspect of the impression in the post.

Bracing of the rearfoot by one means or another has been a popular concept in the treatment of pes plano valgus and other deformities. To understand the biomechanical aspects of the instant invention's rearfoot posting, the theory behind calcaneal control must first be presented.

If a forefoot is abnormally inverted or everted when not bearing weight, when the forefoot strikes the ground, the midtarsal joints and the subtalar joint will compensate for the varus or valgus to allow the entire forefoot to purchase the ground, notwithstanding the deformity. The midtarsal joint, however, has only a limited ability to compensate. The majority of the necessary compensation is done by the subtalar joint. For example, if the forefoot is inverted by 11°, the midtarsal joint may be able to effect only a two or three degree compensation, with the remaining nine to ten degrees being compensated for by subtalar joint pronation.

Compensation by the subtalar joint for a forefoot deformity occurs after the heel strikes the ground. As the forefoot reaches the supporting surface, compensation begins to occur, causing the heel to invert or evert. If the subtalar joint is forced to compensate for an inverted (varus) forefoot, the heel will evert when the forefoot strikes the ground. Likewise, if the subtalar joint is forced to compensate for an everted (valgus) forefoot, the heel will invert when the forefoot strikes the ground. This happens because the midtarsal and subtaler joints function essentially as a unit.

The assessment of whether a foot has a varus or valgus deformity will differ, depending on whether the foot is bearing weight. For example, if the forefoot has a varus deformity when not bearing weight, the heel will evert when the forefoot is placed on the ground and bearing weight. This will cause the heel to appear to have a valgus deformity. Likewise, if the forefoot has a valgus deformity when not bearing weight, the heel will invert when the forefoot is placed on the ground and bearing weight, causing the heel to appear to have a varus deformity.

A majority of orthopedic literature dealing with foot orthoses is based on the control of foot function through the maintenance of the calcaneus around a vertical position in relation to the supporting surface. This theory is based on the concept that the calcaneus cannot be inverted or everted at the subtalar joint without producing subsequent motion around the talonavicular and calcaneocuboid articulations.

By maintaining the calcaneus under the talus and preventing motion from occurring about the subtalar axis, pronation and supination of the rear foot are controlled in both the subtalar and midtarsal joints. These principles were applied into orthoses designed and advocated by Whitman, *Orthopedic Surgery*, 5th Edition, Lea and Febiger, Philadelphia, 1917; Roberts in *The Influence of the Os Calcis on the Production and Correction of Valgus Deformities of the Foot, Am. J. Orthop. Surg.*, December 1916; Schuster, "*Foot Orthopedics*", *First Institute of Podiatry*, New York, 1927; Silverman, *Device for Heel Stabilization, Current Podiatry*, December 1960; and Henderson et al, *UC-BL Shoe Insert: Casting and Fabrication, Bio-Mechanics Research Laboratory, the University of California, San Francisco and Berkley, Technical Report* 53, San Francisco, The Laboratory, August 1967.

Current methods and designs of rearfoot posts may also be traced back to early attempts to control position of the calcaneus. These early attempts will be discussed for comparison with the instant invention in order to understand the mechanisms by which the subtalar joint is controlled in the instant invention.

Heel wedging was the first attempt to control the midstance position of the calcaneus and is in use today as an aid in treatment of foot and gait abnormalities. See, Bick, *Source Book of Orthopedics*, Williams and Wilkins, Baltimore, 1948. Similarly, shoe modifications have been employed. Shoe modifications are gradually falling out of use with the introduction of more efficient orthopedic devices. See, Knittel et al, *The Effectiveness of Shoe Modifications for "In-toeing", Ortho. Clinics*, 7:1019, October 1976; Godfrey, *Heel Modifications as Aids in Rotational Control, Clin. Orthop.*, 4:120, 1954; Wickstrom et al, *Shoe Corrections and Orthopedic Foot Supports, Clin. Orthop.*, 70:30, 1970. Rose describes a modification of what he terms the Schwartz Miniscus which is a wedged, horseshoe-shaped device that fits around the calcaneus, thereby preventing it from inverting or everting to any degree. See, Rose, *Correction of the Pronated Foot, J. Bone Joint Surg.*, 44-B, 142, August 1962. Helfet introduced a laminated shell that encompasses the calcaneus and attempts to contain the calcaneus in a vertical position which is termed a heel seat. Helfet, *A New Way of Treating Flat Feet in Children, Lancet*, 1:262, 1956.

From this discussion, it can be appreciated that extrinsic rearfoot posts of conventional and Root types of functional orthoses are a combination of the design principles incorporated into the heel seat and miniscus. This is represented by the cupping of the thermoplastic around the heel. With extrinsic posting, the thermoplastic around the heel is held in desired position by an acrylic post which is applied extrinsicly to the thermoplastic on the plantar surface of the orthosis to control the calcaneus from heel strike through midstance of the gait cycle. This usually inverts the calcaneus to prevent compensation for a varus deformity.

The rearfoot movable orthosis previously invented by applicant (see Lundeen, 1977, supra) also applies the principles employed above, except rather than the plantar aspect of the acrylic post inverting the rearfoot, the position of the miniscus and heel seat in the frontal plane determines the position around which the calcaneus is to be maintained.

Typically, to make a foot orthosis, a negative impression is first formed of the foot. From the negative impression, a positive casting is made of the foot. A formable material is placed over the casting to conform the formable material generally to the plantar surface of the casting. The formable material is then hardened to a relatively rigid form.

The instant invention represents an improvement in the above-mentioned process. According to the instant invention, the positive casting is sectioned into a main section and a front section. The front section is movable with respect to the main section for correcting deformities in the forefoot. Means are provided for fixing together and adjustably positioning the main section, front section, and rear section. The main section and front section are adjusted with respect to each other to correct for the deformity in the foot. After the sections are adjusted to correct for the deformity, the relative positions of the two sections are fixed with respect to each other.

In one embodiment of the instant invention, the casting can also be sectioned along a line corresponding generally to a line passing obliquely between the fibular and tibial malleoli to form a rear section of the casting. The rear section can then be adjusted to correct for deformities in the rearfoot.

Additionally, the front section of the positive casting can be sectioned generally longitudinally to form a first ray section. The position of the first ray section is then adjusted with respect to the front section to correct for deformities in the forefoot and first ray.

Additionally, a novel positive casting of the human foot for use in making a foot orthosis is provided. The positive casting includes a main section and a front section. The front section is movable with respect to the main section for correcting deformities in the forefoot. Means are provided for fixing together and adjustably positioning the two sections thus formed with respect to each other.

Additionally, the positive casting can include a first ray section which is cut from the front section and is movable with respect to the front section for correcting deformities in the forefoot and first ray.

The polysectional orthosis of the instant invention represents an advance in the construction of orthoses over the rearfoot movable orthosis, which represents the prior, state-of-the-art foot orthosis. To form a rearfoot movable orthosis, a positive casting of a foot is cut along the line which corresponds generally to a line passing obliquely between the fibular and tibial malleoli. After sectioning, the casting includes a main section and a rear section. The rear section is movable with respect to the main section to correct for deformities in the rearfoot. The rearfoot movable orthosis is designed to correct for deformities in the rearfoot by controlling the relative positioning of the heel to the ground.

The polysectional orthosis incorporates a rearfoot movable orthosis' ability to control deformities in the rearfoot and, additionally, controls the joints of the midfoot to control the positioning of the forefoot relative to the ground, thus controlling forefoot deformities. The polysectional orthosis is directed to improving an orthosis' control of the midtarsal joints and the joints of the first ray. The first ray of the foot corresponds generally to the first metatarsal, and the medial cuneiform bone of the foot. The polysectional orthosis, unlike the rearfoot movable orthosis, controls the talonavicular and calcaneal-cuboid joint of the midtarsal joints, the subtalar joint, and the first ray.

In an optional embodiment of the instant invention, the positive casting includes a fourth section which corresponds generally to the first ray of the foot. The use of this first ray section represents the first time that the first ray has been posted independently of the forefoot. The first ray section of the casting is movable with respect to the front section of a casting. This feature has the advantage of making this method of manufacturing an orthotic particularly well-suited to correcting deformities in the first ray. These deformities include situations wherein the first ray of the patient's foot is either abnormally plantar-flexed or abnormally dorsoflexed.

Another advantage of a polysectional casting is that the polysectional casting enables the orthotic manufacturer to adjust the casting to reflect the true condition of the patient's foot. Often, the deformity manifested in the positive casting made of a patient's foot will differ from the deformity measured by the podatrist. This is especially likely in castings made of flat-footed patients. Often, castings made from a flat-footed patient will have the first ray being plantar-flexed with the heel inverted and the forefoot in valgus. In actuality, however, the cast may be falsely representing the true condition of the patient's foot, as flat-footed persons do not normally have everted (valgus) forefoot to rearfoot relationships. With flat-footed persons, the forefoot is usually inverted with respect to the rear foot. This false reading is caused by the action of the peroneous longus around its fulcrum, the cuboid, which causes the first ray to plantar-flex. As a result, the examining podiatrist will often specify that the orthosis be posted in varus, but the casting will be measured in valgus. By sectioning the first ray, and having the front section movable with respect to the midsection of the cast, the orthotic manufacturer can adjust the cast to accurately reflect the measurement taken of the patient's foot by the examining podiatrist.

It is also a feature of the instant invention that the positive casting is sectioned to permit the practitioner to manipulate different sections of the casting independently, thereby enabling the practitioner to manipulate the area of the deformity itself, as manifested in positive casting. By so doing, manifestations of the deformity are manipulated. The manipulation of the manifestations of the deformity are as close as one can get to manipulating the actual deformity itself, short of foot surgery. The instant invention enables the podiatrist and orthotic manufacturer to more accurately capture the deformity in the positive casting, and thereby form an orthosis which corrects for the deformity more accurately than prior art devices.

An optional embodiment of the polysectional orthosis has the additional feature of allowing the physician to post the forefoot independently of the rearfoot. This embodiment of the polysectional orthosis-forming process divides the positive casting into at least three sections: a forefoot section, a rearfoot section, and a main, midfoot section. The midfoot section corresponds generally to the area of the foot adjacent the midtarsal joints. The midfoot section is used as a benchmark around which the forefoot and rearfoot sections of the casting are adjusted. As the rearfoot and forefoot are posted independently with respect to the midfoot section, the posting of the forefoot is independent of the posting of the rearfoot. This feature has the advantage of enabling the physician to form a positive casting which more accurately reflects the true deformity of the foot and form an orthosis which will better correct for the deformity.

Further features and advantages of the instant invention will become apparent to those skilled in the art upon consideration of the following detailed description of a preferred embodiment exemplifying the best mode of carrying out the invention as presently perceived. The detailed description particularly refers to the accompanying figures in which:

In order to appreciate the interaction between the instant invention and the foot, it is necessary to review the bone structure in the foot to understand the relation of the four sections of the positive casting to the structure of the foot, and to understand how the instant invention corrects for foot deformities.

Figure 1:
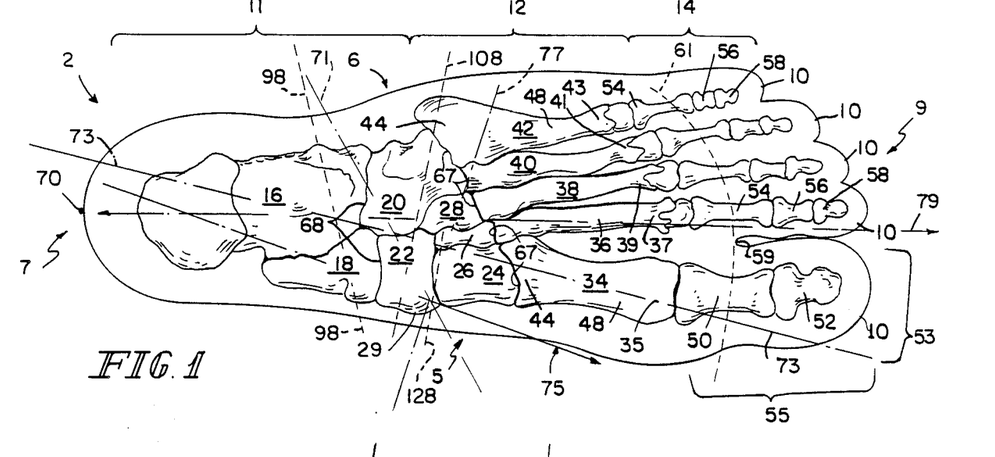
FIG. 1 is a plantar view of the right foot and the bones of the right foot.
Figures 2, 3:
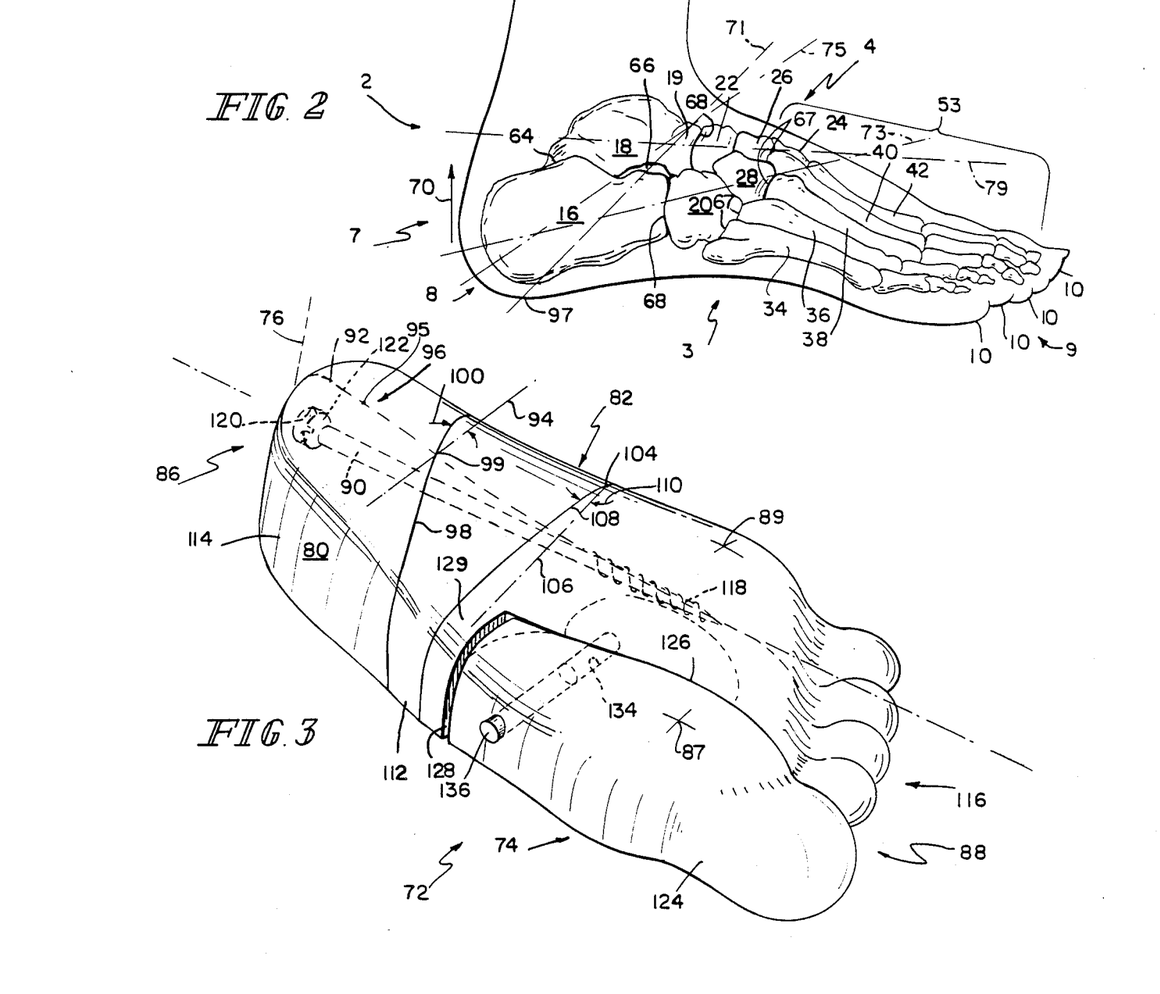
FIG. 2 is a lateral view of the right foot and the bones of the right foot.
FIG. 3 is a perspective, plantar view of the positive casting made of the patient's foot.

A foot 2, shown in FIGS. 1 and 2, has a plantar surface 3, a dorsal surface 4, a medial surface 5, and a lateral surface 6. The proximal end 7 of the foot is that end of the foot 2 near heel 8. The distal end of the foot 2 is that end of the foot near toes 10.

The bones of the foot 2 are divided into three groups: the tarsal bones 11, the metatarsal bones 12, and the phalanges 14. There are seven tarsal bones 11, the calcaneous 16, the talus 18, cuboid 20, navicular 22, medial cuneiform 24, intermediate cuneiform 26, and lateral cuneiform 28. The talus 18 is the second largest of the tarsal bones 11. The head 19 of the talus 18 is located at the distal end of the talus 18. The talus 18 occupies the proximal part of the tarsus 11, supporting the tibia (not shown) resting upon the calcaneus 16 and articulating on the medial side with the medial malleolus (not shown) and on the lateral side with the lateral malleolus (not shown). The calcaneus 16 is the largest of the tarsal bones 11. It is positioned at the posterior part of the foot 2. It forms the heel 8, serving to transmit the weight of the body to the ground, and providing a strong lever for the muscles of the calf (not shown). The cuboid bone 20 is positioned on the lateral side of the foot 8 proximal to two of the metatarsal bones 12. The navicular bone 22 is situated at the medial side of the tarsus 11, between the talus 18 and the cuneiform bones 24, 26, 28. The medial surface of the navicular bone includes a rounded tuberosity, the navicular tuberosity 29, which is used by podiatrists as a benchmark, to mark the apex of the arch (not shown) of the foot 2.

The medial cuneiform bone 24 is the largest of the three cuneiforms 24, 26, 28. It is situated at the medial side of the foot 2, near the navicular 22. The intermediate cuneiform bone 26 is the smallest of the three cuneiform bones 24, 26, 28. The intermediate cuneiform bone 26 has a regular wedge shape, with the thin end being disposed dorsally. The lateral cuneiform bone 28 is intermediate in size between the medial cuneiform bone 24 and the intermediate cuneiform bone 26. It occupies the center of the front row of tarsal bones 11. The intermediate cuneiform bone 26 is located medially of the lateral cuneiform 28, and the navicular bone 22 is located posteriorly of the lateral cuneiform 28.

Metatarsals 12 consist of five bones numbered medially to laterally including first metatarsal 34, second metatarsal 36, third metatarsal 38, fourth metatarsal 40, and fifth metatarsal 42. Each metatarsal 34, 36, 38, 40, 42 includes a head 35, 37, 39, 41, 43, respectively, located at the distal end, a base (e.g., 44) located at the proximal end, and a body (e.g., 48) located therebetween.

Each foot includes fourteen phalanges 14, two phalanges 50, 52 in the hallux 55, and three phalanges in the other four toes 10. The proximal phalanges 54 are those which articulate with the metatarsals 12. The middle row 56 of phalanges are those between the proximal phalanges 54 and the distal row of phalanges 58. The first ray 53 includes the medial cuneiform 24, first metatarsal 34, and the two phalanges 50, 52 of the hallux 55.

Between each pair of toes 10 is an interspace 59 which corresponds to the webbing of tissue between the toes 10. The first interspace is the interspace between the hallux 55 and second toes, the second interspace is between the second and third toes, the third interspace is between the third and fourth toes, and the fourth interspace is between the fourth and fifth toes. The sulcus 61 (FIG. 1) of the toes 10 is an imaginary line corresponding to the bodies of the proximal phalanges 50, 54. On the plantar surface 3 of the foot 2, the sulcus 61 corresponds generally to the concavely curled area of the toes 10. The subtalar joint 64 (talo-calcaneal joint 64) (FIG. 2) is the joint between the plantar surface of the talus 18 and the dorsal surface of the calcaneous 16. The sinus tarsi 66 is a space between the talus 18 and the calcaneous 16 in the general area of the subtalar joint 64. There are two sets of midtarsal joints, the tarso-metatarsal joint 67 and the transverse tarsal (Chopart's) joint 68. The tarso-metatarsal joint 67 includes the joints between the cuneiforms 24, 26, 28, cuboid 20, and metatarsal 34, 36, 38, 40, 42 bases 44. The transverse tarsal (Chopart's) joint 68 includes the joint between the navicular 22 and talus 18 and the joint between the calcaneous 16 and the cuboid 20. Unless otherwise designated, as used herein, "midtarsal joint 68" refers to the transverse tarsal (Chopart's) joint 68. The calcaneal bisection 70, also referred to as the heel bisection 70, is an imaginary plane in the posterior portion of the calcaneous 16 which divides the medial half of the calcaneous 16 from the lateral half of the calcaneous 16, and is often represented as a vertical line bisecting heel 8.

The motion of the foot 2 is largely dictated by anatomical considerations such as the placement, operation, and interaction of the bones, muscles, and connective tissue of the foot 2. Several axes of motion have been identified. Around the oblique midtarsal joint axis 71, the foot 2 will dorsiflex with abduction and plantarflex with adduction. The foot 2 will invert and evert around the long midtarsal joint axis 73. The heel of the foot will generally invert and evert around the axis of the subtalar joint 75. The first ray 53 will mainly dorsiflex with some inversion and plantarflex with some eversion around the axis of first ray 77. The long axis of the foot 79 is not a true resultant axis, but serves primarily as a reference which bisects the foot 2.

To create a foot orthosis according to the instant invention, the first step is to form a negative impression of the foot 2. An indelible pencil is used to mark the medial aspect of the first metatarsal head 35 and the lateral aspect of the fifth metatarsal head 43 of the patient's foot. The calcaneal bisection 70 is also marked. Typically, the practitioner places the patient in a prone position, and places the subtalar joint 64 in a neutral position by palpating for congruency between the head 19 of the talus 18 and the medial and lateral margins of the sinus tarsi 66.

Next, the practitioner grasps the sulcus 61 of the fourth and fifth toe and applies distal traction to the fourth and fifth toes. This serves to dorsoflex the foot 2 to resistance, thereby locking the forefoot on the rearfoot, and serving to neutrally position the midtarsal joint 68 and subtalar joint 64. Plaster splints are then applied to the foot 2 to form a negative impression (not shown) of the foot 2. A conventional two-strip technique can be employed to form the negative impression.

After the plaster splints have dried, the negative impression is slipped off the patient's foot 2 and examined for accuracy by placing a leveling device on top of the impression. The number of degrees from level are noted. The result thus obtained from the measurement of the level of the negative impression is compared with the measurement taken by the podiatrist of the patient's forefoot in the biomechanical examination. The difference between the two readings will indicate the amount of forefoot varus or valgus that has been captured in the negative impression. The reading obtained in the negative impression should be within 2° of that obtained by a biomechanical examination performed on the patient.

From the negative impression, a positive casting 72 is made in the following way. The negative impression is dipped in a separating solution such as soap. The separating solution facilitates the removal of the positive casting 72 from the negative impression. The negative impression is placed with its plantar surface on a level table. The forefoot is wedged in order to bring the heel bisection 70 to vertical. The heel bisection of the negative impression is brought to vertical so that the dorsal surface 74 of the positive casting 72 will be perpendicular to the heel bisection 76 of the casting 72. The dorsal surface 74 of the positive casting 72 is preferably perpendicular to the heel bisection 76 of the casting to facilitate the manipulation of the casting 72 to correct for the deformities.

The positive casting 72 is made of plaster, which is mixed in the usual manner, poured into the negative impression, and allowed to harden. When set, the plaster splints of the negative impression are stripped from the positive casting 72. The positive casting 72 is lightly wet-sanded to remove imperfections and any separating agents.

Positive casting 72 corresponds generally in size and shape to a patient's foot 2 from which it is made. In the discussion herein of the positive casting 72, the parts of the positive casting 72 are labeled with names which correspond to the analogous parts of the patient's foot 2.

A perspective view of the positive casting 72 is shown in FIGS. 3-6 wherein casting 72 is placed upon its dorsal surface 74. Positive casting 72 also includes a plantar surface 78, a medial surface 80, a lateral surface 82, a proximal end 86, and a distal end 88.

After the plaster of the positive casting 72 is hardened, the dorsal surface 74 of the positive casting 72 is placed on a level supporting surface. The bisections of the first metatarsal head 87 and fifth metatarsal head 89 are marked on the plantar surface 78 of the casting 72. A longitudinal hole 90 approximately ¼ inch (0.635 cm) in diameter is drilled from the proximal end 86 distally through the casting 72 to a point approximately equal to an imaginary line coextensive with the bisections of the metatarsal heads 87, 89. A pencil is used to mark the position of the calcaneal bisection 76 on the proximal end 86 surface of the casting 72. Using the calcaneal bisection 76 as a guide, a longitudinal line 92, partially coextensive with calcaneal bisection 76, is drawn on the plantar surface 78 of the casting 72, following the contour of the plantar surface 78 of the casting. A rear benchmark line 94 is drawn perpendicularly to longitudinal line 92 at a place corresponding generally to the forepart of the heel 96 of the casting 72.

Benchmark line 94 is normally drawn approximately 1 inch (2.54 cm) distally of heel contact point 95. The heel contact point 95 is the highest point on the heel 96 portion of the plantar surface 78 of the casting 72. The heel contact point 95 of casting 72 corresponds generally on the foot 2 to the lowest point 97 of the heel 8 of the foot 2. A spot 99 which represents the intersection of line 92 and benchmark line 94 is marked. First, axis 98 is cut laterally across casting 72 to correspond generally to a line rotated at an 18° angle 100 counterclockwise from benchmark line 94 using spot 99 as the axis of rotation. This results in first axis 98 having its furthest proximal extent at lateral side 82, and its furthest distal extent at medial side 80 of positive casting 72.

First axis 98 corresponds generally to a line passing obliquely between the fibular and tibial malleolei of the foot. The 18° angle 100 at which the first axis is cut is chosen because it is oblique to the axis of the subtalar joint 75 (FIG. 1), and also takes into consideration the normal value of malleolar torsion in adults.

A spot 104 corresponding to the base 44 of the fifth metatarsal 42 (FIG. 1) is marked. From this spot 104, a main section benchmark line 106 is drawn perpendicular to longitudinal line 92. Second axis 108 is cut at an angle 110 approximately 18° from midsection benchmark line 106 directed medially and proximally. Second axis 110 corresponds generally to a line passing parallel to the space between the navicular tuberosity, and the prominence of the fifth metatarsal 42 base 44 and is oblique to the longitudinal axis of the midtarsal joint 73.

After the first axis 98 and second axis 108 have been cut, positive casting 72 is separated into three sections 112, 114, 116. Main section 112 corresponds generally to that section of the foot adjacent the midtarsal joint 68. Rear section 114 corresponds generally to that section of the foot to adjacent to and proximal of the subtalar joint 64, and is movable with respect to main section 112. Front section 116 corresponds generally to that section of the foot to adjacent and distal to the navicular 22 and cuboid 20 bones and is also movable with respect to the main section 112.

After the sections 112, 114, 116 have been separated, a shaft means such as screw 118 is inserted into longitudinal hole 90 through rear section 114 and main section 112 and anchored into front section 116. The longitudinal extension of screw 118 is adjustable to bring the main section 112 of rear section 114 and front section 116 into and out of frictional engagement. The longitudinal hole 90 may include a widened portion 120 to accommodate a screw head 122 having a larger diameter than the shaft portion of the screw. Additionally, a MOLLY BOLT type fastener can be inserted into the portion of the longitudinal hole 90 in front section 116 to serve as an anchor for the threads of the screw 118.

In an alternate embodiment, screw 118 can be replaced by a shaft means such as a dowel rod (not shown) having no threads. In such case, the three sections of the casting 112, 114, 116 are rotatable about the axis of the rod. Plaster is added in the area adjacent the first axis 98 and the second axis 108 to fix the relative position of the three sections 112, 114, 116 with respect to each other.

A fourth, first ray section 124 can be formed from a portion of front section 116. The first ray section 124 is separated from and medial to first section 116. To form first ray section 124, front section 116 is cut along a third line 126 which corresponds generally to a line between the first ray and the second ray, extending generally from the lateral aspect of the medial cuneiform-navicular joint distally to the distal end 88 of the casting 72. The third axis 128 is made perpendicular to third line 126 at the proximal end of third line 126 just in the front area of the cast corresponding to the navicular tuberosity 29 (FIG. 1). The dorsal and plantar aspects of the proximal end 129 of the first ray section 124 of casting 72 are rounded to facillate rotation dorsally and plantarly of the first ray section 124.

An aperture 134 is drilled laterally through first ray section 124 and into front section 116. A peg 136 is inserted into the aperture 134 to enable the first ray section 124 to move with respect to front section 116. When peg 136 is inserted, the first ray section 124 can move dorsally or plantarly about the axis formed by peg 136. The first ray section 124 is movable with respect to the first section for correcting deformity in the first ray of the foot, or in the forefoot itself. First ray section 124 is also movable to enable the orthotic manufacturer to adjust the casting 72 to reflect the true deformity of the foot in a flat-footed person.

After casting 72 has been sectioned, the main section 112, the rear section 114, the front section 116, and first ray section 124 are moved with respect to each other to compensate for the deformity. The normal procedure for posting the casting 72 is that screw 118 is loosened to permit main section 112, rear section 114, and front section 116 to rotate with respect to each other. The positive casting 72 is then placed with its dorsal surface 74 up and its plantar surface 78 resting upon a level supporting surface. The rear section 114 and main section 112 are rotated until the calcaneal bisection 76 is perpendicular to the level supporting surface upon which the casting 72 rests. The forefoot section 116 is then rotated to a point at which the bisections of the first and fifth metatarsal heads 87, 89 are resting upon the level supporting surface. Alternatively, the first ray section 124 can be moved either dorsally or plantarly to a point where the first metatarsal head bisection 87 is resting upon the level supporting surface. It is preferable to drop the first ray section 124 to ground, rather than rotating the front section 116 in cases where the forefoot deformity is not that great. In situations wherein the forefoot deformity is more extreme, it is preferable to rotate the front section 116, or to move the first ray section 124 along with rotating front section 116.

After the forefoot has been posted by moving the first ray section 124 or rotating the front section 116 or both, the rear section 114 is posted. A level is placed upon the dorsal surface 74 of the rear section 116 to ensure that the calcaneal bisection 76 is at vertical. From this point, the rear section 14 is rotated in varus or valgus to the number of degrees from vertical specified in the podiatrist's prescription to correct for deformity in the rearfoot. The main section 112 should lie in the same plane as the supporting surface after the forefoot and rearfoot have been posted.

Figures 4, 5:
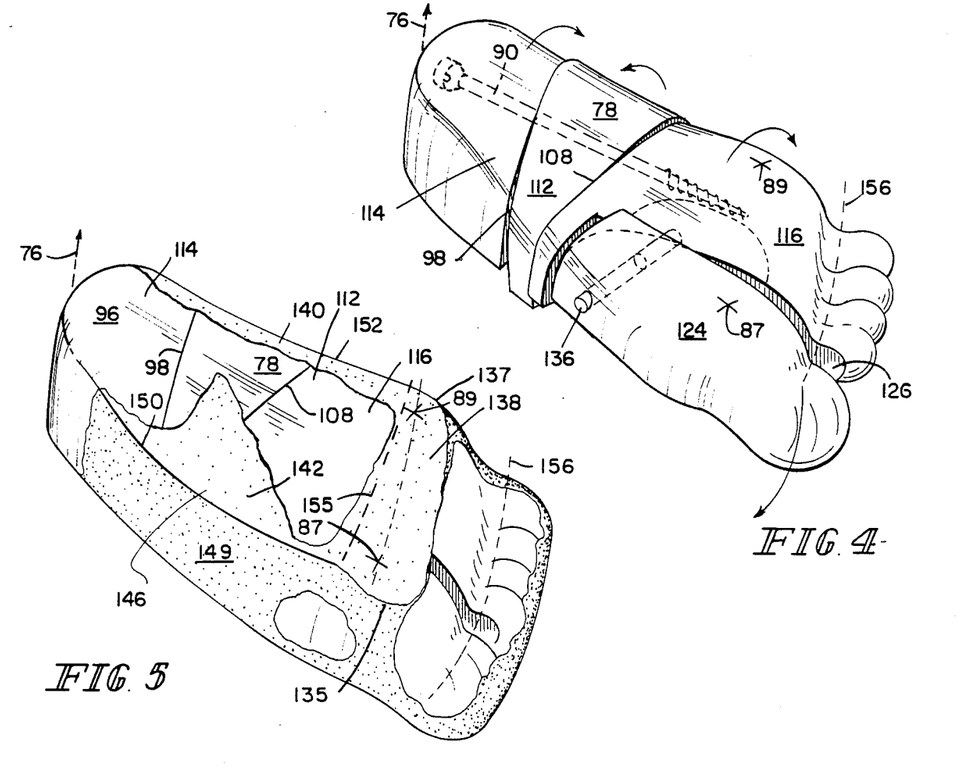
FIG. 4 is a perspective, plantar view of the positive casting wherein the sections of the casting are rotated to correct for the deformities of the foot.
FIG. 5 is a perspective, plantar view of the positive casting with a moldable material added to its surface.

A hypothetical adjustment of the casting is shown in FIG. 4 wherein first ray section 124 has been moved dorsally with respect to front section 116, front section 116 has been rotated in valgus with respect to main section 112, main section 112 has been rotated in varus with respect to front section 116, and rearfoot section 114 has been rotated in valgus with respect to main section 112.

After the sections 112, 114, 116, and 124 of the casting 72 have been moved with respect to each other to correct for the deformities in the foot, the relative positioning of the sections 112, 114, 116, 124 of casting 72 is fixed in place. In positive castings 72 having a screw 118 inserted through aperture 90, the positions are fixed by tightening screw 118 in its anchor in front section 116. In positive castings 72 using a dowel rod, the positions of sections 112, 114, 116, 124 are fixed by applying plaster onto the surface of the casting 72 in the areas of the casting 72 adjacent first axis 98 and second axis 108. The position of first ray section 124 is fixed with respect to front section 116 by applying plaster in the area of the casting 72 adjacent third axis 128 and third line 126.

At this juncture, it is convenient to apply plaster to the dorsal surface 74 of the casting 72 to fill in any gaps caused by the rotation of the sections 112, 114, 116, 124 of the casting 72. Approximately ½ inch (1.27 cm) of plaster is applied to the dorsal surface 74 of casting 72 to ensure that the dorsal surface 74 will be level. A moldable material such as plaster is also added to the plantar surface 78 of the casting 72 to form a plantar platform 138, a lateral expansion 140, and a medial expansion 142. Conventionally, the plantar platform 138 is formed by making a pile of wet plaster on a level surface, and by placing the portion of the casting adjacent to metatarsal head bisections 87, 89 into the plaster to form a planar surface on the area of the positive casting 72 adjacent to the metatarsal head bisections 87, 89. In conventional castings, the plantar platform was used as a post to invert or evert the forefoot.

In the instant invention, the plantar platform 138 is not used for posting. The plantar platform 138 is used to square up the medial 135 and lateral corners 137 of the casting 72, and to fill in inconsistencies, if necessary, in the area of the plantar surface 78 of casting 72 between metatarsal head bisections 87, 89. To form the plantar platform 138 of the instant invention, a moldable material such as plaster is placed on the casting 72 with a spatula or similar article, vertical to the medial 80 side of the casting, and laterally on the plantar surface 78 of the casting to the area of the plantar surface 78 at or near the first metatarsal head bisection 87. Plaster is also applied in a similar manner vertical to the lateral side 82 of the casting and medially on the plantar surface 78 of the casting 72 to the area of the plantar surface 78 at or near the fifth metatarsal head bisection 89. If necessary, a thin layer of plaster is then applied to the plantar surface 78 between the bisections of the first 87 and fifth 89 metatarsal heads.

The plantar platform 138 also serves to level the medial and lateral borders of the positive casting, thereby forming a planar surface on the forefoot, plantar surface 78 of the cast. After the plaster in the plantar platform 138 has dried, it is sanded to form a level plateau over the plantar surface 78 extending from the first metatarsal head bisection 87 to the fifth metatarsal head bisection 89, with the expansion being approximately 1 inch (2.54 cm) to 1¼ inch (3.17 cm) in width. If necessary, the bisections of the first and fifth metatarsal heads 87, 89 are remarked on the plantar platform 138.

Lateral expansion 140 is formed through the addition of a moldable material such as plaster along the lateral edge of the casting 72, extending from the plantar platform 138 in the area adjacent the metatarsal heads proximally to the area two to three centimeters from the calcaneal bisection 76. The lateral expansion 140 should not exceed 5 to 8 millimeters in thickness, and is added to increase the width of the casting 72, and hence increase the width of an orthosis 148 formed from the casting 72, to reflect the width of the foot 2 when the foot 2 is bearing weight. Since the casting 72 is made from a negative impression which is taken when the foot 2 is not bearing weight, the plantar surface 3 of the foot 2 will not be as wide as it will be when the foot 2 is bearing weight. This increase in width is due to the expansion of the plantar fat pads of the foot 2 when the foot 2 is bearing weight. Hence, the plantar surface 78 of the casting 72 will be narrower than the plantar surface 3 of the weight-bearing foot 2. The lateral expansion 140 is added to provide, in a finished orthosis 148, a supporting surface which is wide enough to accommodate this increased width.

Medial expansion 142 is added on the medial edge of the casting 80 and in the area of the casting 72 corresponding to the arch 146 of the foot 2. The widening of the plantar surface by the medial expansion 142 prevents the medial border 164 of the orthosis 148 from jamming the arch 146 of the foot when undergoing normal function in gait. Also, plaster is added on the plantar surface 78 of the casting 72 in the area corresponding to the arch 146 of the foot 2 to smooth the transition on the medial side of the plantar surface 78 of the casting 72 from the area of the navicular tuberosity 29 distal to the metatarsal heads 35, 37, 39 as far lateral as the fourth metatarsal head 41 (FIG. 1). In adding plaster to the arch 146, the contours of the adjusted casting 72 should maintain the plane of the plantar surface 3 of the foot 2. When viewing the casting 72 with its plantar surface 78 up, the lowest portion of the arch 146 will normally be the area of the plantar surface 78 on the main section 112 of the casting 72 which corresponds to the area around the navicular tuberosity 29 of the foot 2. The highest portion of the medial side of the plantar surface 78 of the casting 72 will normally be the area of the casting 72 which corresponds to the heel 96 of the casting 72 and the bisections of the metatarsal heads 87, 89.

The plaster applied for the medial expansion 142 will generally not extend to the highest portion of the heel 96. The depth of the plaster will generally be tapered, meeting the plaster of the plantar surface 78 of the casting 72 in the area near the forepart of the medial section of the heel 96. The plantar surface of the medial expansion 142 should follow the contour of the plantar surface 78 of the casting 72. The plaster added for the medial expansion 142 should serve the aforementioned purposes without causing an excess amount of plaster to build up on the plantar surface 78 of the casting 72.

The plaster added to form the medial 142 and lateral 140 expansions should be great enough to make the plantar surface 78 of the casting 72 as wide or wider than the plantar surface 3 of the foot 2 when bearing weight. This is necessary to ensure that the lateral and medial edges of the foot 2 will not be extending over the side edges of the finished orthosis 148. If the medial and lateral edges of the foot do extend over the side, the orthotic 148 is likely to irritate the foot when the patient is walking. This results in the patient suffering discomfort from the use of the orthosis 148. The lateral 140 expansion is added to the positive casting 72 to prevent this discomfort. Further, if plaster is not added to the medial, plantar surface 78 of the positive casting 72 to smooth the transition level between the heel 96, arch 146, and metatarsal head bisection 87, the patient's foot 2 will also likely be irritated.

It is also possible, with some castings 72, to form a smooth transition in the plantar surface 78 of the casting 72 by rasping the plantar surface 78 of the casting 72 in the area adjacent the first 98, second 108, and third 128 axes, rather than adding plaster to the plantar surface 78. The choice of whether to rasp portions of the plantar surface 78 to form a smooth transition, or to add plaster to form a smooth transition, is dictated largely by the particular rotation of the sections 112, 114, 116, 124 called for in the prescription, and the difference in the levels between the sections 112, 114, 116, 124.

The medial and lateral expansions should be rasped distally to the distal trim line 155 of the casting 72. The distal trim line 155 of the positive casting 72 is found by marking a spot on the casting 72 approximately 1/16 to ⅛ inch (0.16 to 0.32 cm) behind the fifth metatarsal head bisection 89 and ⅛ to ¼ inch (0.635 to 1.27 cm) behind the first metatarsal head bisection 87. The distal trim line 155 is then drawn between the two marked spots in a line parallel to the toe sulcus 156. Experimentation has shown that the distal trim line 155 is closely parallel to the curve of the metatarsal heads 35, 37, 39, 41, 43 of foot 2. The use of distal trim line 155 enables the podiatrist to determine the location of the most proximal portion of the metatarsal heads 35, 37, 39, 41, 43 on the positive casting 72 of the foot 2.

After the medial 142, lateral 140, and plantar 138 expansions have been added to the casting 72, the medial 80 and lateral 82 sides of the casting are sanded to bring the lateral 82 and medial 80 sides of the casting 72 perpendicular to the dorsal surface 74 of the casting 72. The medial 80 and lateral 82 sides of the casting 72 are also sanded to form creases 150, 152 at the intersection of the plantar 78 surface and medial side 149 of the casting 72, and at the intersection of the plantar surface 78 and the lateral side 82 of the casting 72.

Figure 6:
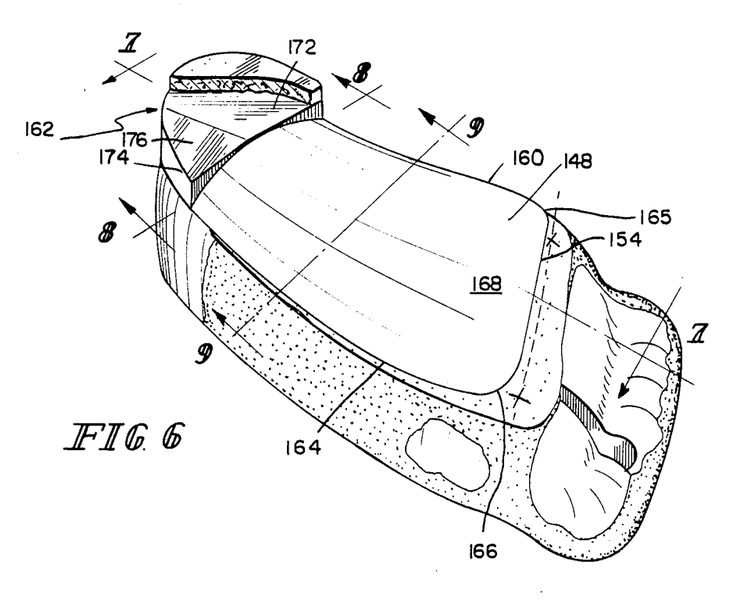
FIG. 6 is a perspective view of an orthotic formed according to the instant invention overlaying the positive casting.

The casting 72 is then wet-sanded lightly to remove imperfections and to smooth the plantar 78 surface of the casting 72. The orthosis 148 is formed from a formable material such as a thermoplastic which is vacuum or mechanically pressed over the plantar surface 78 of the casting 72. One material which has been found to work well is CYRODUR-O acrylic thermoplastic which is distributed by Cyro Industries, Clifton, N.J. The thermoplastic is preferably supplied in sheet form approximately 3 to 5 mm thick. Blanks (not shown) are cut from the thermoplastic sheet to have a semicircular proximal end and a squared-off distal end and be approximately 4 to 5 inches (10.16 to 12.7 cm) wide. After the blank is formed or pressed over the plantar surface 78 of the casting 72, it should conform exactly to the contour of the plantar surface of the positive casting 72. The thermoplastic blank is allowed to harden on the casting 72 to impart a relatively rigid form to the formable thermoplastic blank. The blank, after hardening, is then finished to remove undesirable aberrations to form the orthosis 148.

The thermoplastic blank which is formed over the casting 72 will normally be larger than the finished orthosis 148. The blank must usually be cut to the proper size. The distal edge 154 of the orthosis 148 is cut to the distal trim line 155 of the positive casting 72. The lateral edge 160 of the orthosis 148 is cut in a straight line from its intersection of lateral with the distal edge 154 of the orthosis 148 to the beginning of the rounded portion of the heel 162 of the orthosis 148. Similarly, the medial edge 164 of the orthosis 148 is cut from the intersection of the medial edge 164 and distal edge 154 from the first metatarsal head bisection 87 straight back to the medial aspect of the beginning of the rounded portion of the heel 162. The intersection of the medial edge 164 and distal edge 154 of the orthosis will normally be approximately ⅛ inch to ¼ inch (0.625 cm to 1.27 cm) directly behind the bisection of the first metatarsal head 87. The heel portion 162 of the orthosis is rounded to form a semicircular proximal (heel) edge of the orthosis 148. The distal, lateral 165 and distal medial 166 corners are also rounded slightly. The edges of the orthosis 148 may then, if necessary, be ground or sanded to remove undesirable aberations.

The orthosis 148 is turned with its dorsal surface downward and its plantar surface 168 upward. A piece of masking tape is placed laterally across the orthosis 148 from the medial edge 164 to the lateral edge 160 approximately 1 inch distal to the heel contact point 170. The heel contact point 170 is the highest point on the plantar surface 168 of the orthosis 148 in the heel area 162. The plantar surface 168 of the orthosis 148 proximal to the masking tape is roughened using a rough grinding wheel. Standard clear dental acrylic is mixed in the usual manner and placed on a level surface. The heel portion 162 of the plantar surface 168 of orthosis 148 is then placed in the acrylic to form heel post 172. The heel post serves to prevent the heel 8 of the foot 2 from inverting or everting. Absent the addition of heel post 172, the heel contact point 170 would provide only a one-point contact for a heel 162 portion of the orthosis 148 with the ground. Side surface 174 of the heel post 172 is then trimmed to conform with the edges 160, 164 of the orthosis 148. The distal-medial ⅛ 176 of the plantar surface of the heel post 172 is then skived approximately 4 to 6 degrees from horizontal to allow for heel 8 pronation which normally occurs during midstance.

Figure 7:
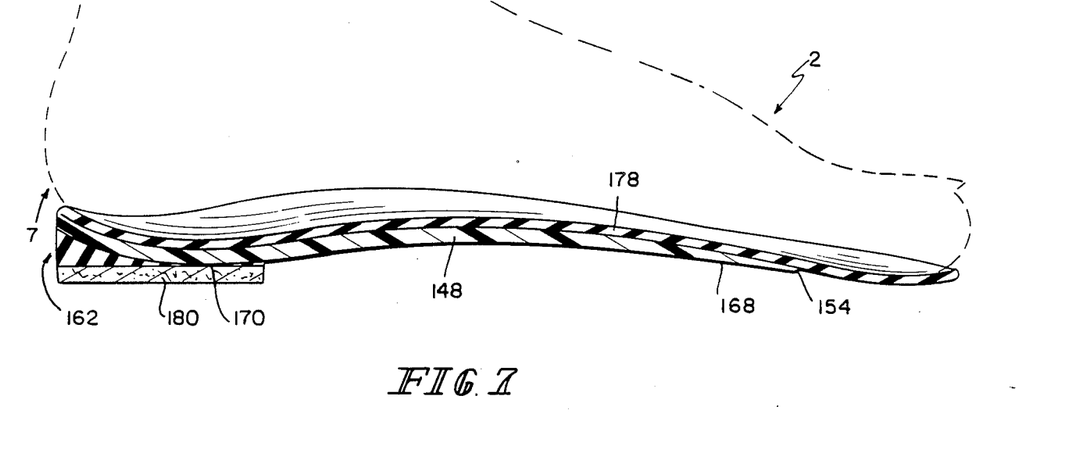
FIG. 7 is a cross-sectional view taken along lines 7—7 of FIG. 6.
Figure 8:
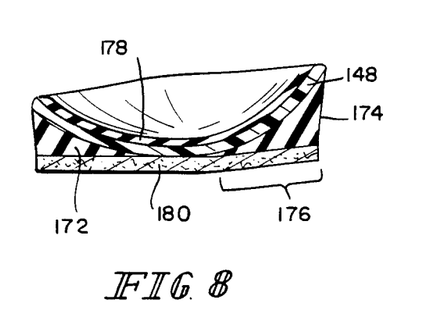
FIG. 8 is a cross-sectional view taken along lines 8—8 of FIG. 6.
Figure 9:
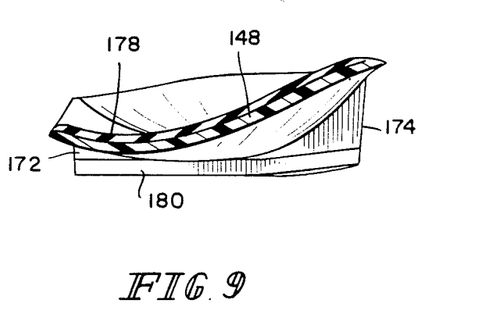
FIG. 9 is a cross-sectional view taken along lines 9—9 of FIG. 6.

After the orthosis 148 has been ground finely, it may be buffed using any available method. This improves the asthetic value of the device and provides a finishing touch. Additionally, the orthosis 148 can be provided with a vinyl or leather top covering 178 which extends past the distal end 154 of the orthosis 148 substantially the full length of the foot 2. A layer of cushioning material 180 such as a cork-polyethylene blended material can be placed under the heel post 172 to provide additional cushioning under the heel 8 and reduce the severity of shock during heel strike.

Although the invention has been described in detail with reference to certain preferred embodiments, methodologies, and specific examples, variations and modifications exist within the scope and spirit of the invention as described and as defined in the following claims.

What is claimed is:

1. A positive casting of a human foot for use in making a foot orthosis comprising
a main section, a rear section, a front section, and a long axis generally parallel to the long axis of the foot,
said main section defined generally by that section of the foot adjacent the midtarsal joint,
said rear section separated from said main section by a plane generally transverse to said long axis, said rear section being defined generally by that section of the foot adjacent to and proximal of the subtalar joint, the rear section section being rotatable about said long axis for movement with respect to the main section for correcting deformities in the rearfoot,
said front section separated from said main section by a plane generally transverse to said long axis, said front section being defined generally by that section of the foot adjacent and distal of the navicular and cuboid bones, the front section being rotatable about said long axis for movement with respect to the main section for correcting deformities in the forefoot, and
means for fixing the relative positions of said main, rear, and front sections.

2. The invention of claim 1 wherein said means for fixing the relative positions comprises a shaft means which defines said long axis, said shaft means being insertable into the main section, rear section, and front section, and being adjustable to bring the three sections into and out of frictional engagement.

3. The invention of claim 1 further comprising a first ray section separated from said front section by a plane generally parallel to said long axis and a plane generally transverse to said long axis, said first ray section being defined generally by the section of the foot corresponding to the medial cuneiform, first metatarsal and the phalanges of the hallux, the first ray section being movable with respect to the front section for correcting deformities in the forefoot and first ray.

4. In a positive casting of a human foot for use in making a foot orthosis, the improvement comprising
a long axis generally parallel to the long axis of the foot,
a front section defined generally by that section of the foot adjacent to and distal of the navicular and cuboid bones of the foot, said front section being separated from said main section by a plane generally transverse to said long axis, and
a first ray section separated from said front section by a plane generally transverse to said long axis and a plane generally parallel to said long axis, said first ray section being movable in a dorsal and plantar direction with respect to the front section for correcting deformities in the forefoot and first ray of the foot,
the first ray section defined generally by that section of the foot corresponding to the medial cuneiform, first metatarsal, and the phalanges of the hallux.

5. The improvement of claim 4 further comprising a shaft means operatively connecting the first ray section with the positive casting, the first ray section being movable dorsally and plantarly about the axis formed by the shaft.

6. A positive casting of a human foot for use in making a foot orthosis comprising
a main section, a front section and a long axis generally parallel to the long axis of the foot,
said front section being separated from said main section by a plane generally transverse to said long axis, said front section being defined generally by that section of the foot adjacent and distal of the navicular and cuboid bones of the foot, the front section being rotatably movable with respect to the main section about said long axis for correcting deformities in the forefoot, and means for fixing the relative positions of said front and main sections with respect to one another.

7. The invention of claim 6 further comprising a rear section rotatable about said long axis means for movement with respect to the main section for correcting deformities in the rearfoot.

8. A positive casting of a human foot for use in constructing a foot orthosis comprising four separable sections including a main section defined generally by the foot arches, a front section defined generally by the ball and toe area of the foot, a rear section defined generally by the heel of the foot, and a first ray section defined generally by the medial cuneiform, first metatarsal and phalanges of the hallux, said front section and said rear section being rotatably movable with respect to said main section about an axis extending in a direction generally parallel to a line corresponding to a line extending between the heel and toes of the foot, and said first ray section being movable with respect to said front section in a generally dorsal and plantar direction.

9. A positive casting of a human foot for use in constructing a foot orthosis comprising at least two sections, the sections including a first ray section defined generally by the medial cuneiform, first metatarsal and the phalanges of the hallux, and at least one other section defined generally by a section of the foot other than that section of the foot defined by the first ray section, the first ray section being separated from said at least one other section by a generally longitudinally extending plane and by a generally transverse plane, said first ray section being movable in a dorsal and plantar direction relative to the at least one other section.

* * * * *